United States Patent
Bovin et al.

(10) Patent No.: US 9,494,515 B2
(45) Date of Patent: Nov. 15, 2016

(54) GLYCAN ARRAYS AND METHODS FOR THEIR FABRICATION

(75) Inventors: Nikolay Vladimirovich Bovin, Moscow (RU); Nadezhda Vladimirovna Shilova, Moscow (RU)

(73) Assignee: Obschestvo s organichennoy oivetstvennostyu "SEMIOTIK", Moscow (RU)

( * ) Notice: Subject to any disclaimer, the term of this patent is extended or adjusted under 35 U.S.C. 154(b) by 423 days.

(21) Appl. No.: 13/977,202

(22) PCT Filed: Dec. 30, 2010

(86) PCT No.: PCT/RU2010/000813
§ 371 (c)(1),
(2), (4) Date: Jun. 28, 2013

(87) PCT Pub. No.: WO2012/091606
PCT Pub. Date: Jul. 5, 2012

(65) Prior Publication Data
US 2013/0288928 A1    Oct. 31, 2013

(51) Int. Cl.
*G01N 21/64* (2006.01)
*G01N 33/533* (2006.01)
*A61K 49/00* (2006.01)
*C07H 15/04* (2006.01)
(Continued)

(52) U.S. Cl.
CPC ....... *G01N 21/6428* (2013.01); *A61K 49/0043* (2013.01); *A61K 49/0054* (2013.01); *C07H 15/04* (2013.01); *C07H 15/12* (2013.01); *G01N 33/533* (2013.01); *G01N 33/54393* (2013.01); *G01N 2400/40* (2013.01)

(58) Field of Classification Search
CPC ........... G01N 21/6428; G01N 33/533; G01N 33/54393; G01N 2400/40; A61K 49/0043; A61K 49/0054; C07H 15/04; C07H 15/12
See application file for complete search history.

(56) References Cited

U.S. PATENT DOCUMENTS
2008/0076137 A1    3/2008    Bovin et al.

FOREIGN PATENT DOCUMENTS
WO    WO 2005/088310 A2    9/2005

OTHER PUBLICATIONS
Hessner et al. (Nucleic Acids Research, 2003, 31(11):e60 pp. 1-9).*
Tateno et al. (Glycobiology, 2008, 18(10):789-798).*
(Continued)

*Primary Examiner* — Jeremy C Flinders
(74) *Attorney, Agent, or Firm* — Collard & Roe, P.C.

(57) ABSTRACT

The invention relates to glycan arrays with quantified levels of glycan expression and a method for fabricating thereof. The method comprises quantitatively reacting an ω-aminoalkylglycan with an activated polymer of an acrylic acid derivative to obtain glycoconjugated polymer or copolymer and covalently attaching the (co)polymer to a functionalized substrate. The glycan arrays according to the invention comprise an co-aminoalkylglycan covalently attached to a functionalized substrate via a fluorescently labeled (co) polymer of an acrylic acid derivative. The copolymer of the acrylic acid derivative may comprise fluorescein cadaverine as a fluorescent label or lysine or aminated PEG. The functionalized substrate is selected from an epoxylated and aminated glass or plastic. The invention also provides a fluorescently labeled co-aminoalkylglycan conjugated polymer of the acrylic acid derivative for use in the fabrication of glycan arrays.

22 Claims, 4 Drawing Sheets

(51) Int. Cl.
*C07H 15/12* (2006.01)
*G01N 33/543* (2006.01)

(56) References Cited

OTHER PUBLICATIONS

Taki et al. (Protein Engineering, Design & Selection, 2004, 17(2):119-126).*
International Search Report of PCT/RU2010/000813, Oct. 6, 2011.
Bovin N.V., Polyacrylamide-based glycoconjugates as tools in glycobiology, Glycoconjugate Journal, 1998, vol. 15, No. 5, pp. 431-446.
Shilova N.V., (2005) High molecular weight neoglycoconjugates for solid phase assays, Glycoconjugate Journal, 2005, 22, pp. 43-51.
Dyukova V.I. et al., Design of carbohydrate multiarrays, Biochimica et Biophysica Acta 2006, 1760, pp. 603-609.
Blixt et al, (2004) Printed covalent glycan array for ligand profiling of diverse glycan binding proteins, Proc Nat. Aca. Sc. US 101, Dec. 7, 2004, 17033-17038.
Bovin et al, (1993) Synthesis of polymeric neoglycoconjugates based on N-substituted polyacrylamides, Glycoconjugate Journal, 10, 142-151.
Adalsteinsson et al,(1979) Preparation and magnetic filtration of polyacrylamide gels containing covalently immobilized proteins and a ferrofluid, J Molec Catalysis 6, 199-225.
Jacob et al., The glycosphingolipid P1 is an ovarian cancer-associated carbohydrate antigen involved in migration, British Journal of Cancer, published online Aug. 28, 2014, pp. 1634-1645, vol. 111, UK, DOI: 10.1038/bjc.2014.455.

* cited by examiner

GLYCAN ARRAYS AND METHODS FOR THEIR FABRICATION

CROSS REFERECNE TO RELATED APPLICATIONS

This application is the National Stage of PCT/RU2010/000813 filed on Dec. 30, 2010. The international application under PCT article 21 (2) was published in English.

FIELD OF INVENTION

The invention relates to glycan arrays and methods for their fabrication. In particular, the invention relates to glycan arrays with quantified levels of glycan expression and a method for their fabrication.

BACKGROUND ART

The quantitative assessment of ligands binding to glycan targets characteristic of various pathologies, including cancer, is an essential aspect of accurate diagnosis. Unreliable quantitative assessment of ligand binding may result in misdiagnosis and consequential negative impacts on patient wellbeing. Glycan arrays have been developed for the purpose of assessing ligand binding to glycans. A glycan array consists of an array of glycans deposited, typically in the form of dots, on a substrate.

The routine fabrication of glycan arrays requires a range of putative glycan targets to be deposited [Blixt and Head (2005) High throughput glycan inicroarrays Publ. no. WO 2005/088310; Blixt et al (2004) *Printed covalent glycan array for ligand profiling of diverse glycan binding proteins* Proc Nat. Aca. Sc. US 101, 17033-17038].

The different glycans may be deposited with differing efficiencies and yields and therefore requires quantification before the glycan array can be used reliably and routinely in diagnosis. For automated high throughput screening the fabrication of the glycan arrays must also be consistent in terms of dot location (predetermined locus) and morphology. Variations in these parameters will result in an inability to assess ligand binding by automated systems.

The foregoing problems are particularly relevant in the context of diagnosing pathologies where the quantitative assessment of a range of glycan binding ligands is required. These problems are further exacerbated by glycan binding ligands participating in multivalent interactions with their ligand targets. It is an object of the present invention to provide an improved method of fabricating glycan arrays or to at least a useful choice.

STATEMENT OF INVENTION

In a first aspect the invention provides a method of fabricating a glycan array comprising the steps of:
1. Quantitatively reacting an ω-aminoalkylglycan with an activated polymer of an acrylic acid derivative to provide a glycoconjugated polymer or copolymer of an acrylic acid derivative; and
2. Covalently attaching the glycoconjugated polymer or copolymer of an acrylic acid derivative to a functionalised substrate.

Preferably, the ω-aminoalkylglycan is selected from the group consisting of: ω-aminoalkyl O- or N-derivatives of a glycan. More preferably, the ω-aminoalkylglycan is selected from the group consisting of: ω-amino-$C_{1-6}$-alkyl O- or N-derivatives of a glycan. Most preferably, the ω-amino-$C_{1-6}$-alkyl O- or N-derivatives of a glycan is selected from the group consisting of: Glyc-$OCH_2CH_2CH_2NH_2$, Glyc-$OCH_2CH_2NH_2$ and Glyc-$NHCOCH_2NH_2$.

Preferably, the glycan (Glyc) is selected from the group consisting of: Galα, Glcα, Manα, GalNAcα, Fucα, Rhaα, Neu5Acα, Neu5Acα, Neu5Acβ, Galβ, Glcβ, Manβ, GalNAcβ, GlcNAcβ, GlcNAcβ, GlcNGcβ, Galβ1-4GlcNAcβ1-3(Galβ1-4GlcNAcβ1-6)GalNAcα, GlcNAcβ1-3(GlcNAcβ1-6)GlcNAcβ1-4GlcNAcβ, Gal[3OSO₃, 6OSO₃]β1-4GlcNAc[6OSO₃]β, Gal[3OSO₃, 6OSO₃]β1-4GlcNAcβ, Gal[3OSO₃]β1-4Glcβ, Gal[3OSO₃]β1-4Glc[6OSO₃]β, Gal[3OSO₃]β1-4Glc[6OSO₃]β, Gal[3OSO₃]β1-3(Fucα1-4)GlcNAcβ, Gal[3OSO₃]β1-3GalNAcα, Gal[3OSO₃]β1-3GlcNAcβ, Gal[3OSO₃]β1-4(Fucα1-3)GlcNAcβ, Gal[6OSO₃]β1-4GlcNAcβ[6OSO₃]β, Gal[3OSO₃]β1-4GlcNAcβ, Gal[3OSO₃]β1-4GlcNAcβ, Gal[3OSO₃]β, Gal[4OSO₃, 6OSO₃]β1-4GlcNAc, Gal[4OSO₃]β1-4GlcNAcβ, Man[6-H2PO3]α, Gal[6OSO₃]β1-4Glcβ, Gal[6OSO₃]β1-4Glcβ, Gal[6OSO₃]β1-4GlcNAcβ, Gal[6OSO₃]β1-4Glc[6OSO₃]β, Neu5Acα2-3Gal[6OSO₃]β1-4GlcNAcβ, GlcNAc[6OSO₃]β, Neu5Ac[9Ac]α, Neu5Ac[9Ac]α2-6Galβ1-4GlcNAcβ, Manα1-3 (Manα1-6)Manβ1-4GlcNAcβ1-4GlcNAcβ, GlcNAcβ1-2Manα1-3 (GlcNAcβ1-2Manα1-6)Manβ1-4GlcNAcβ1-4GlcNAcβ, Galβ1-4GlcNAcβ1-2Manα1-3 (Galβ1-4GlcNAcβ1-2Manα1-6)Manβ1-4GlcNAcβ1-4GlcNAcβ, Neu5Acα2-3Galβ1-4GlcNAcβ1-2Manα1-3(Neu5Acα2-3Galβ1-4GlcNAcβ1-2Manα1-6)Manβ1-4GlcNAcβ1-4GlcNAcβ, Neu5Acα2-6Galβ1-4GlcNAcβ1-2Manα1-3(Neu5Acα2-6 Galβ1-4GlcNAcβ1-2Manα1-6)Manβ1-4GlcNAcβ1-4GlcNAcβ, Fucα1-2Galβ1-3GalNAcβ1-3Galα, Fucα1-2Galβ1-3GalNAcβ1-3Galα1-4Galβ1-4Glcβ, Fucα1-2Galβ1-3(Fucα1-4)GlcNAcβ, Fucα1-2Galβ1-3GalNAcα, Fucα1-2Galβ1-3GalNAcβ1-4(Neu5Acα2-3)Galβ1-4Glcβ, Fucα1-2Galβ1-3GalNAcβ1-4(Neu5Acα2-3)Galβ1-4Glcβ, Fucα1-2Galβ1-3GlcNAcβ1-3Galβ1-4Glcβ, Fucα1-2Galβ1-3GlcNAcβ1-3Galβ1-4Glcβ, Fucα1-2Galβ1-3GlcNAcβ, Fucα1-2Galβ1-3GlcNAcβ, Fucα1-2Galβ1-4(Fucα1-3)GlcNAcβ1-3Galβ1-4(Fucα1-3)GlcNAcβ, Fucα1-2Galβ1-4 (Fucα1-3)GlcNAcβ1-3Galβ1-4(Fucα1-3)GlcNAcβ1-3Galβ1-4(Fucα1-3)GlcNAcβ, Fucα1-2Galβ1-4(Fucα1-3)GlcNAcβ, Fucα1-2Galβ1-4(Fucα1-3)GlcNAcβ, Fucα1-2Galβ1-4GlcNAcβ1-3Galβ1-4GlcNAcβ, Fucα1-2Galβ1-4GlcNAcβ1-3Galβ1-4GlcNAcβ1-3Galβ1-4GlcNAcβ, Fucα1-2Galβ1-4GlcNAcβ, Fucα1-2Galβ1-4GlcNAcβ, Fucα1-2Galβ1-4Glcβ, Fucα1-2Galβ, Fucα1-2GlcNAcβ, Fucα1-3GlcNAcβ, Fucα1-4GlcNAcβ, Fucα1-3GlcNAcβ, GalNAcα1-3(Fucα1-2)Galβ1-3GlcNAcβ, GalNAcα1-3(Fucα1-2)Galβ1-4(Fucα1-3)GlcNAcβ, GalNAcα1-3(Fucα1-2)Galβ1-4GlcNAcβ, GalNAcα1-3 (Fucα1-2)Galβ1-4GlcNAcβ, GalNAcα1-3(Fucα1-2)Galβ1-4Glcβ, GalNAcα1-3(Fucα1-2)Galβ, GalNAcα1-3GalNAcβ, GalNAcα1-3Galβ, GalNAcα1-4(Fucα1-2)Galβ1-4GlcNAcβ, GalNAcβ1-3GalNAcα, GalNAcβ1-3 (Fucα1-2)Galβ, GalNAcβ1-3Galα1-4Galβ1-4GlcNAcβ, GalNAcβ1-4(Fucα1-3)GlcNAcβ, GalNAcβ1-4GlcNAcβ, GalNAcβ1-4GlcNAcβGalα1-2Galβ, Galα1-3(Fucα1-2)Galβ1-3GlcNAcβ, Galα1-3(Fucα1-2)Galβ1-4(Fucα1-3)GlcNAcβ, Galα1-3(Fucα1-2)Galβ1-4GlcNAcβ, Galα1-3 (Fucα1-2)Galβ1-4Glcβ, Galα1-3(Fucα1-2)Galβ, Galα1-3 (Galα1-4)Galβ1-4GlcNAcβ, Galα1-3GalNAcα, Galα1-3GalNAcβ, Galα1-3Galβ1-4(Fucα1-3)GlcNAcβ, Galα1-3Galβ1-3GlcNAcβ, Galα1-3Galβ1-4GlcNAcβ, Galα1-3Galβ1-4Glcβ, Galα1-3Galβ, Galα1-4(Fucα1-2)Galβ1-4GlcNAcβ, Galα1-4Galβ1-4GlcNAcβ, Galα1-4Galβ1-4GlcNAcβ, Galα1-4Galβ1-4Glcβ, Galα1-4GlcNAcβ, Galα1-6Glcβ, Galβ1-2Galβ, Galβ1-3(Fucα1-4)GlcNAcβ1-

3Galβ1-4(Fucα1-3)GlcNAcβ, Galβ1-3(Fucα1-4) GlcNAcβ1-3Galβ1-4GlcNAcβ, Galβ1-3(Fucα1-4) GlcNAcβ, Galβ1-3(Fucα1-4)GlcNAcβ, Galβ1-3(Fucα1-4) GlcNAcβ, Galβ1-3 (Galβ1-4GlcNAcβ1-6)GalNAcα, Galβ1-3 (GlcNAcβ1-6)GalNAcα, Galβ1-3(Neu5Acα2-6) GalNAcα, Galβ1-3(Neu5Acβ2-6)GalNAcα, Galβ1-3 (Neu5Acα2-6)GlcNAcβ1-4Galβ1-4Glcβ, Galβ1-3GalNAcα, Galβ1-3GalNAcβ, Galβ1-3GalNAcβ1-3Galα1-4Galβ1-4Glcβ, Galβ1-3GalNAcβ1-4(Neu5Acα2-3)Galβ1-4Glcβ, Galβ1-3GalNAcβ1-4Galβ1-4Glcβ, Galβ1-3Galβ, Galβ1-3GlcNAcβ1-3Galβ1-4GlcNAcβ, Galβ1-3GlcNAcβ1-3Galβ1-4Glcβ, Galβ1-3GlcNAcβ, Galβ1-3GlcNAcβ, Galβ1-4 (Fucα1-3)GlcNAcβ, Galβ1-4(Fucα1-3)GlcNAcβ, Galβ1-4Glc[6OSO₃]β, Galβ1-4Glc[6OSO₃]β, Galβ1-4GalNAcα1-3(Fucα1-2)Galβ1-4GlcNAcβ, Galβ1-4GalNAcβ1-3(Fucα1-2)Galβ1-4GlcNAcβ, Galβ1-4GlcNAcβ1-3 (Galβ1-4GlcNAcβ1-6)GalNAcα, Galβ1-4GlcNAcβ1-3GalNAcα, Galβ1-4 GlcNAcβ1-3Galβ1-4(Fucα1-3)GlcNAcβ1-3Galβ1-4(Fucα1-3)GlcNAcβ, Galβ1-4GlcNAcβ1-3Galβ1-4GlcNAcβ, Galβ1-4GlcNAcβ1-3Galβ1-4Glcβ, Galβ1-4GlcNAcβ1-3Galβ1-4Glcβ, Galβ1-4GlcNAcβ1-6(Galβ1-3)GalNAcα, Galβ1-4GlcNAcβ1-6GalNAcα, Galβ1-4GlcNAcβ, Galβ1-4GlcNAcβ, Galβ1-4Glcβ, Galβ1-4Glcβ, GlcNAcβ1-3Galβ1-4GlcNAcβ, GlcNAcα1-6Galβ1-4GlcNAcβ, GlcNAcβ1-2Galβ1-3GalNAcα, GlcNAcβ1-3(GlcNAcβ1-6)GalNAcα, GlcNAcβ1-3(GlcNAcβ1-6)Galβ1-4GlcNAcβ, GlcNAcβ1-3GalNAcα, GlcNAcβ1-3Galβ, GlcNAcβ1-3Galβ1-3GalNAcα, GlcNAcβ1-3Galβ1-4GlcNAcβ, GlcNAcβ1-3Galβ1-4GlcNAcβ, GlcNAcβ1-3Galβ1-4GlcNAcβ1-3Galβ1-4GlcNAcβ, GlcNAcβ1-3Galβ1-4Glcβ, GlcNAcβ1-4MDPLys (bacterial cell wall), GlcNAcβ1-4(GlcNAcβ1-6)GalNAcα, GlcNAcβ1-4Galβ1-4GlcNAcβ, GlcNAcβ1-4GlcNAcβ1-4GlcNAcβ1-4GlcNAcβ1-4GlcNAcβ, GlcNAcβ1-4GlcNAcβ1-4GlcNAcβ1-4GlcNAcβ1-4GlcNAcβ, GlcNAcβ1-4GlcNAcβ1-4GlcNAcβ, GlcNAcβ1-6(Galβ1-3)GalNAcα, GlcNAcβ1-6GalNAcα, GlcNAcβ1-6Galβ1-4GlcNAcβ, Glcα1-4Glcβ, Glcα1-4Glcα, Glcα1-6Glcα1-6Glcβ, Glcβ1-4Glcβ, Glcβ1-6Glcβ, GlcAα, GlcAβ, GlcAβ1-3Galβ, GleAβ1-6Galβ, KDNα2-3Galβ1-3GlcNAcβ, KDNα2-3Galβ1-4GlcNAcβ, Manα1-2Manα1-2Manα1-3Manα, Manα1-2Manα1-3(Manα1-2Manα1-6)Manα, Manα1-2Manα1-3Manα, Manα1-6(Manα1-2Manα1-3)Manα1-6(Manα1-2Manα1-3)Manβ1-4GlcNAcβ1-4GlcNAcβ, Manα1-2Manα1-6(Manα1-3)Manα1-6(Manα1-2Manα1-2Manα1-3)Manβ1-4GlcNAcβ1-4GlcNAcβ, Manα1-2Manα1-2Manα1-3[Manα1-2Manα1-3(Manα1-2Manα1-6)Manα1-6]Manβ1-4GlcNAcβ1-4GlcNAcβ, Manα1-3(Manα1-6)Manα, Manα1-3(Manα1-2Manα1-2Manα1-6)Manα, Manα1-2Manα1-3(Manα1-3(Manα1-6)Manα1-6)Manβ1-4GlcNAcβ1-4GlcNAcβ, Manα1-3(Manα1-3(Manα1-6)Manα1-6)Manβ1-4GlcNAcβ1-4GlcNAcα, Manβ1-4GlcNAcβ, Neu5Acα2-3(Galβ1-3GalNAcβ1-4)Galβ1-4Glcβ, Neu5Acα2-3Galβ1-3GalNAcα, Neu5Acα2-8Neu5Acα2-8Neu5Acα2-8Neu5Acα2-3(GalNAcβ1-4)Galβ1-4Glcβ, Neu5Acα2-8Neu5Acα2-8Neu5Acα2-3(GalNAcβ1-4)Galβ1-4Glcβ, Neu5Acα2-8Neu5Acα2-8Neu5Acα2-3Galβ1-4Glcβ, Neu5Acα2-8Neu5Acα2-3(GalNAcβ1-4)Galβ1-4Glcβ, Neu5Acα2-8Neu5Acα2-8Neu5Acα, Neu5Acα2-3Gal[6OSO₃]β1-4(Fucα1-3)GlcNAcβ, Neu5Acα2-3(GalNAcβ1-4)Galβ1-4GlcNAcβ, Neu5Acα2-3(GalNAcβ1-4)Galβ1-4GlcNAcβ, Neu5Acα2-3(GalNAcβ1-4)Galβ1-4Glcβ, Neu5Acα2-3Galβ1-3GalNAcβ1-4)Galβ1-4Glcβ, Neu5Acα2-3(Neu5Acα2-6)GalNAcα, Neu5Acα2-3GalNAcα, Neu5Acα2-3GalNAcβ1-4GlcNAcβ, Neu5Acα2-3Gal[6OSO₃]β1-3GlcNAc, Neu5Acα2-3Galβ1-3(Fucα1-4) GlcNAcβ, Neu5Acα2-3Galβ1-3(Fucα1-4)GlcNAcβ1-3Galβ1-4(Fucα1-3)GlcNAcβ, Neu5Acα2-3Galβ1-3(Neu5Acα2-3Galβ1-4)GlcNAcβ, Neu5Acα2-3Galβ1-3GalNAc[6OSO₃]α, Neu5Acα2-3(Neu5Acα2-6)GalNAcα, Neu5Acα2-3Galβ, Neu5Acα2-3Galβ1-3GalNAcβ1-3Galβ1-4Galβ1-4Glcβ, Neu5Acα2-3Galβ1-3GalNAcβ1-3Galβ1-4GlcNAcβ, Neu5Acα2-3Galβ1-3GlcNAcβ, Neu5Acα2-3Galβ1-3GlcNAcβ, Neu5Acα2-3Galβ1-4GlcNAc[6OSO₃]β, Neu5Acα2-3Galβ1-4(Fucα1-3)GlcNAc[6OSO₃]β, Neu5Acα2-3Galβ1-4(Fucα1-3)GlcNAcβ1-3Galβ1-4(Fucα1-3) GlcNAcβ, Neu5Acα2-3Galβ1-4(Fucα1-3)GlcNAcβ, Neu5Acα2-3Galβ1-4(Fucα1-3)GlcNAcβ, Neu5Acα2-3Galβ1-4(Fucα1-3)GlcNAcβ1-3Galβ, Neu5Acα2-3Galβ1-4(Fucα1-3)GlcNAcβ1-3Galβ1-4GlcNAcβ, Neu5Acα2-3Galβ1-4GlcNAcβ1-3Galβ1-4(Fucα1-3)GlcNAc, Neu5Acα2-3Galβ1-4GlcNAcβ1-3Galβ1-4GlcNAcβ1-3Galβ1-4GlcNAcβ, Neu5Acα2-3Galβ1-4GlcNAcβ, Neu5Acα2-3Galβ1-4GlcNAcβ1-3Galβ1-4GlcNAcβ, Neu5Acα2-3Galβ1-4GlcNAcβ1-3Galβ1-4GlcNAcβ, Neu5Acα2-3Galβ1-4Glcβ, Neu5Acα2-3Galβ1-4Glcβ, Neu5Acα2-6(Galβ1-3) GalNAcα, Neu5Acα2-6GalNAcα, Neu5Acα2-6GalNAcβ1-4GlcNAcβ, Neu5Acα2-6Galβ1-4GlcNAc[6OSO₃]β, Neu5Acα2-6Galβ1-4GlcNAcβ, Neu5Acα2-6Galβ1-4GlcNAcβ, Neu5Acα2-6Galβ1-4GlcNAcβ1-3Galβ1-4(Fucα1-3)GlcNAcβ1-3Galβ1-4(Fucα1-3) GlcNAcβ, Neu5Acα2-6 Galβ1-4GlcNAcβ1-3Galβ1-4GlcNAcβ, Neu5Acα2-6Galβ1-4Glcβ, Neu5Acα2-6Galβ1-4Glcβ, Neu5Acα2-6Galβ, Neu5Acα2-8Neu5Acα, Neu5Acα2-8Neu5Acα2-3Galβ1-4Glcβ, Neu5Acβ2-6GalNAcα, Neu5Acβ2-6Galβ1-4GlcNAcβ, Neu5Acβ2-6(Galβ1-3)GalNAcα, Neu5Gcα2-3Galβ1-3(Fucα1-4) GlcNAcβ, Neu5Gcα2-3Galβ1-3GlcNAcβ, Neu5Gcα2-3Galβ1-4(Fucα1-3)GlcNAcβ, Neu5Gcα2-3Galβ1-4GlcNAcβ, Neu5Gcα2-3Galβ1-4Glcβ, Neu5Gcα2-6GalNAcα, Neu5Gcα2-6Galβ1-4GlcNAcβ and Neu5Gcα.

Preferably, the activated polymer of an acrylic acid derivative is selected from the group consisting of: poly(4-nitrophenyl acrylate) and poly(N-oxysuccinimidyl acrylate).

Preferably, the glycoconjugated polymer or copolymer of an acrylic acid derivative is fluorescently labelled. More preferably, the fluorophore of the fluorescent label is selected from the group consisting of: fluorophores of fluorescein. Most preferably, the fluorescent label is selected from the group consisting of: fluorescein cadaverine (fluo).

Preferably, the glycoconjugated polymer or copolymer of an acrylic acid derivative comprises fluorophore at no more than 1 mole %.

Preferably, the glycoconjugated polymer or copolymer of an acrylic acid derivative comprises glycan in the range 0.1 to 20 mole %.

Preferably, the covalently attaching is via a plurality of bonds.

Preferably, the functionalised substrate is selected from the group consisting of: aminated and epoxylated substrates.

Preferably, the substrate is selected from the group consisting of: glass and plastic. More preferably, the substrate is selected from the group consisting of: glass and plastic slides.

In the second aspect the invention provides a glycan array comprising ω-aminoalkylglycan covalently attached to a functionalised substrate via a polymer or copolymer of an acrylic acid derivative.

Preferably, the glycan array comprises ω-aminoalkylglycan covalently attached to a functionalised substrate via a copolymer of an acrylic acid derivative of the formula:

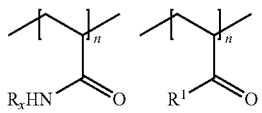

where x is an integer from 1 to n and $R_x$ is selected from the alkylglycan and at least one from the group consisting of: lysine, aminated PEG or substrate; $R^1$ is $NH_2$, OH or $HOCH_2CH_2NH$.

Preferably, the glycoconjugated polymer of an acrylic acid derivative is fluorescently labelled. More preferably, the fluorophore of the fluorescent label is selected from the group consisting of: fluorophores of fluorescein. Most preferably, the fluorescent label is selected from the group consisting of fluorescein cadaverine (fluo).

Preferably, the glycoconjugated polymer of an acrylic acid derivative comprises fluorophore at no more than 1 mole %.

Preferably, the glycoconjugated polymer of an acrylic acid derivative comprises glycan in the range 0.1 to 20 mole %.

Preferably, the covalently attaching is via a plurality of bonds.

Preferably, the functionalised substrate is selected from the group consisting of: aminated and epoxylated substrates.

Preferably, the substrate is selected from the group consisting of: glass and plastic. More preferably, the substrate is selected from the group consisting of: glass and plastic slides.

In a first embodiment of the second aspect the invention provides a glycan array comprising ω-aminoalkylglycan covalently attached to an aminated substrate via a fluorescently labelled copolymer of an acrylic acid derivative of the formula:

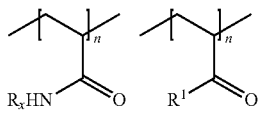

where x is an integer from 1 to n and $R_x$ is either the alkylglycan, fluorescein cadaverine (fluo) or the substrate; $R^1$ is $NH_2$, OH or $HOCH_2CH_2NH$.

In a second embodiment of the second aspect the invention provides a glycan array comprising ω-aminoalkylglycan covalently attached to a functionalised substrate via a fluorescently labelled copolymer of an acrylic acid derivative of the formula:

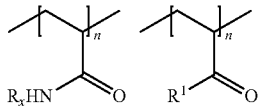

where x is an integer from 1 to n and $R_x$ is either the alkylglycan, fluorescein cadaverine (fluo) or aminated PEG and the functionalised substrate is an epoxylated substrate; R1 is $NH_2$, OH or $HOCH_2CH_2NH$.

In a third embodiment of the second aspect the invention provides a glycan array comprising ω-aminoalkylglycan covalently attached to a functionalised substrate via a fluorescently labelled copolymer of an acrylic acid derivative of the formula:

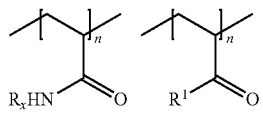

where x is an integer from 1 to n and $R_x$ is either the alkylglycan, fluorescein cadaverine (fluo) or lysine and the functionalised substrate is an epoxylated substrate; $R^1$ is $NH_2$, OH or $HOCH_2CH_2NH$.

In a third aspect the invention provides a fluorescently labelled, ω-aminoalkylglycan conjugated polymer of an acrylic acid derivative packaged and identified for use in the fabrication of glycan arrays where the polymer is of the formula:

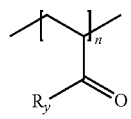

x is an integer from 1 to n and $R_y$ is selected from ω-aminoalkylglycan and at least one from the group consisting of: 4-nitrophenyl, N-oxysuccinimidyl, lysine and aminated PEG.

Preferably, the fluorophore of the fluorescent label is selected from the group consisting of: fluorophores of fluorescein. Most preferably, the fluorescent label is selected from the group consisting of: fluorescein cadaverine (fluo).

Preferably, the glycoconjugated polymer of an acrylic acid derivative comprises fluorophore at no more than 1 mole %.

Preferably, the glycoconjugated polymer of an acrylic acid derivative comprises glycan in the range 0.1 to 20 mole %.

In the description and claims of this specification the following acronyms, terms and phrases have the meaning provided: "BSA" means bovine serum albumin; "CHAPS" means 3-[(3-cholamidopropyl)dimethylammonio]-1-propanesulfonate; "Covalently" means a chemical bond is formed in which two or more atoms are held together by the interaction of their nuclei with one or more pairs of electrons and specifically excludes the bond formed between biotin and avidin or streptavidin; "DMF" means dimethylformamide; "DMSO" means dimethyl sulfoxide; "$Et_3N$" means triethylamine; "Fluorophore" means a chemical moiety which will absorb energy of a specific wavelength and re-emit energy at a different wavelength; "Fluorescently labelled" means a fluorophore derivative is covalently attached and "fluorescently labelling" has a corresponding meaning; "Glass substrate" means a glass slide or other such substrate that has a glass surface; "Glycan array" means a substrate on which glycans are deposited at a plurality of discrete and predetermined locations; "m.w." means molecular weight; "$pNPA^{30}$" means 30 kDa poly(4-nitrophenyl acrylate); "$pNSA^{2000}$" means 2000 kDa poly(N-oxysuccinimidyl acrylate); "PAA" means poly(N-2-hydroxyethyl acrylamide); "$A_{tri}$" means GalNAcα1-3(Fucα1-2)Gal; "$B_{tri}$" means Galα1-3(Fucα1-2)Gal; "fluo" means fluorescein cadaverin residue; "Glyc" and "glycan" mean a mono-, di-, tri- or oligo-saccharide residue; "OS" means oligosaccharide; "PEG" means polyethyleneglycol; "Polymer of an acrylic acid derivative" means a polymer of the formula:

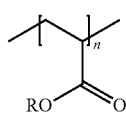

where R is other than H and n is the median polymer number (mer);

"Copolymer" means a polymer of formula

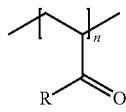

where R are two or more different substituents.

"Quantitative reaction" means a reaction in which the yield of product as a percentage of the theoretical maximum is substantially the same over a range of concentrations of the reagent(s) from which the product is derived (and "quantitatively reacting" has a corresponding meaning) and "ω-aminoalkylglycan" means an aminoalkyl derivative of a glycan having a primary amino group, including Glyc-OCH$_2$CH$_2$CH$_2$NH$_2$, Glyc-OCH$_2$CH$_2$NH$_2$ and Glyc-NHCOCH$_2$NH$_2$.

The terms "first", "second", "third", etc. used with reference to elements, features or integers of the subject matter defined in the Statement of Invention and Claims, or when used with reference to alternative embodiments of the invention are not intended to imply an order of preference. The invention will now be described with reference to embodiments or examples and the figures of the accompanying drawings pages.

DETAILED DESCRIPTION

Figure 1:
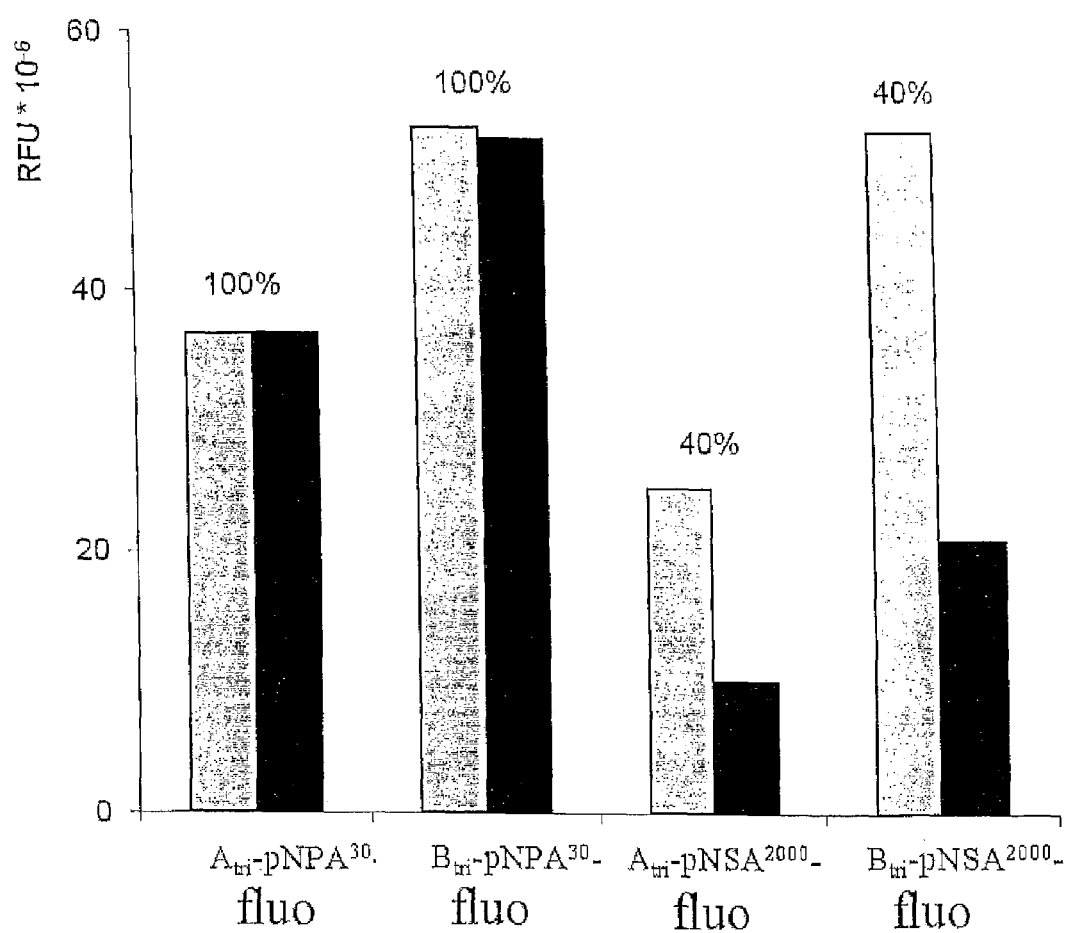
FIG. 1. Comparison of the fluorescent signal ratios before (light shading) and after (dark shading) washing following immobilization of fluorescently labelled, ω-aminoalkylglycan derivatised activated polyacrylic acid.
Figure 2:
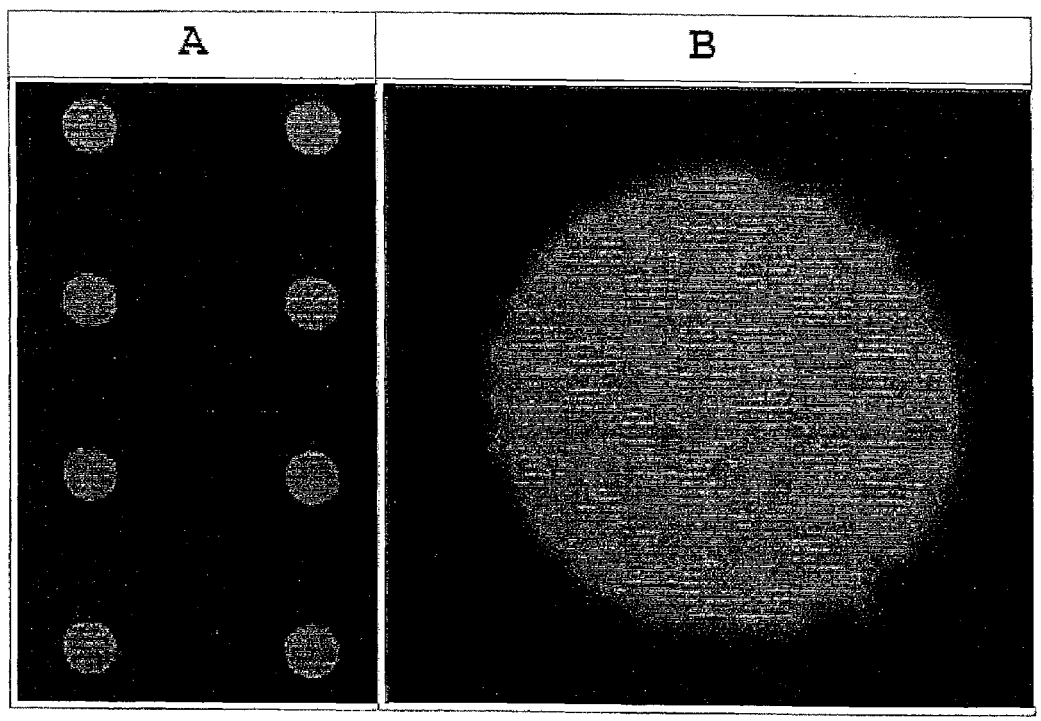
FIG. 2. Microfluorograph of glycan array following immobilization of fluorescently labelled, ω-aminoalkylglycan derivatised activated polyacrylic acid at a plurality of discrete and predetermined locations (8 spots). The glycan array was scanned after final washing (magnification: ×50 (A) and ×150 (B)).
Figure 3:
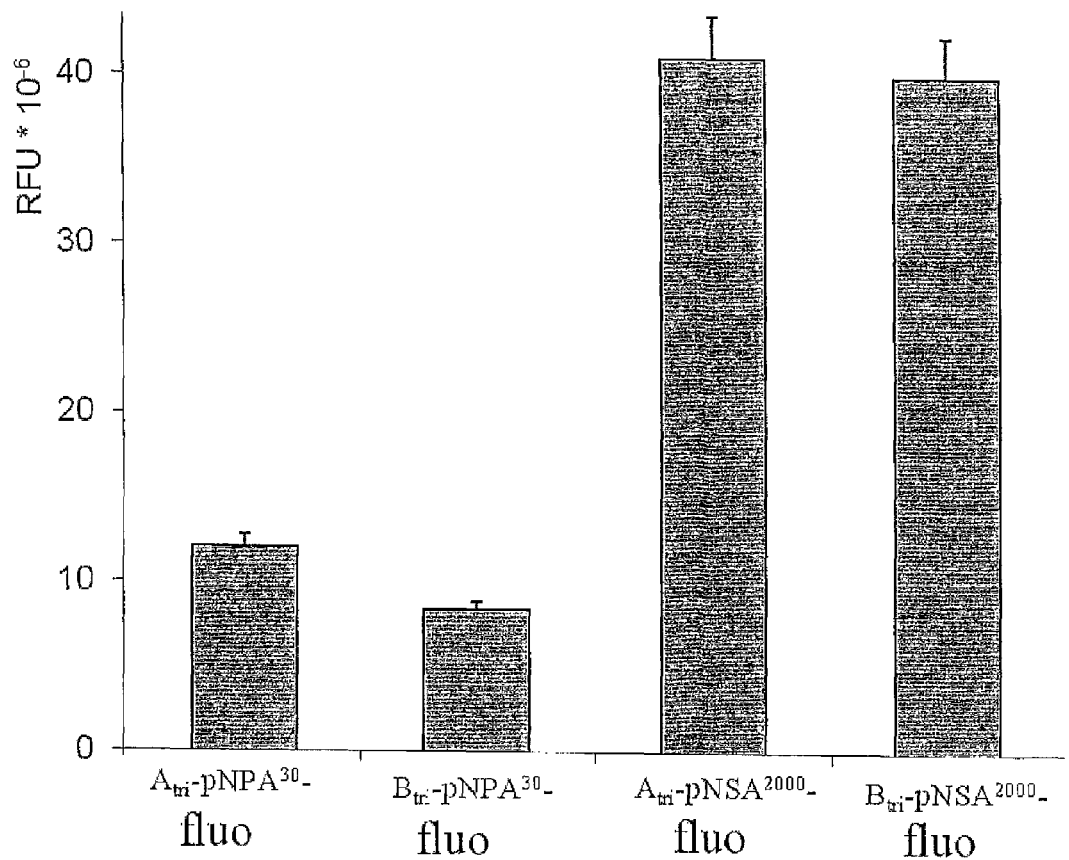
FIG. 3. Binding of antibodies of healthy donor serum (blood group 0) with immobilized A$_{tri}$-PAA$^{30}$-fluo, B$_{tri}$-PAA$^{30}$-fluo, A$_{tri}$-PAA$^{2000}$-fluo, and B$_{tri}$-PAA$^{2000}$-fluo. Glycan array development was performed using fluorescently labelled secondary antibodies. Background (signal from dots containing polyacrylamide without carbohydrate ligands) was subtracted.

The invention resides in the covalent attachment of a fluorescently labelled glycopolymer to a functionalized substrate by a two-step method. The method permits the quantitative attachment of glycan to polymers, followed by the quantitative attachment of glycopolymer to substrate. The method of the invention permits the attachment of glycans to the substrate to be controlled under conditions which are not deleterious to the functionality (glycan and fluorophore) of the glycopolymer. The use of an amidated or epoxylated substrate provides a glycan array with a uniform background; absent the undesired inconsistencies and reactivities of avidinylated substrates. The method provides greater control of attachment of the glycans to a predetermined locus than is obtainable using known attachment methods. Although some of the problems of the known methods may be overcome by incorporation of a fluorescent label into the glycopolymer and normalization of assay results, as suggested by Bovin and Chinarev (2008) [Bioanalytic systems and methods Publ. no. US2008/00766137], the quantitative deposition of target glycans on a substrate by covalent bonding is preferred.

EXAMPLES

Materials and Methods

BSA, Tween™ 20, DMSO, Et$_3$N, AcOH and ethanolamine were from Sigma-Aldrich (USA). Spacer-connected oligosaccharides were from Lectinity (Moscow, Russia). Fluorescein-cadaverine was from Molecular probes (USA). AlexaFluor™ 647 goat anti-human IgG (H+L) and IgM (0.1 chain) were from Invitrogen™ (USA). Aminated UltraGAPS™ glass slides were from Corning (USA). Vantage epoxy-activated slides were from CEL Associates (USA), pNPA$^{30}$ [Bovin et al (1993) *Synthesis of polymeric neoglycoconjugates based on N-substituted polyacrylamides Glycoconjugate Journal*, 10, 142-151] and pNSA$^{2000}$ [Adalsteinsson et al (1979) *Preparation and magnetic filtration of polyacrylamide gels containing covalently immobilized proteins and a ferrofluid* J Molec Catalysis 6, 199-225] were synthesized as described by these authors. Samples of serum from healthy donors, were obtained from Sklifosovsky Emergency Medicine Institute (Moscow, Russian Federation). Intravenous IgG was from LFB (France). Plant lectins were from Vector Labs (USA). Aminated PEG (2 kDa) was from IRIS Biothech (Germany).

Synthesis of Fluorescein-Containing Glycoconjugates

Example 1

Derivatives of N-Hydroxysuccinimide-Activated Polyacrylic Acid

A solution of 5.1 mg (30 mg-eq.) pNSA$^{2000}$ in 500 μl DMSO was added to 0.3 μmol of fluorescein-cadaverine in 44 μl of DMSO followed by 6 μl triethylamine and incubated at 37° C. overnight. The mixture was then divided into 3 equal aliquots identified as #1, #2 and #3. Nothing was added to aliquot #1 (negative control). 1.1 mg (2 μmol) of B$_{tri}$—OCH$_2$CH$_2$CH$_2$NH$_2$ in 500 μl DMSO containing additional 5 μl of triethylamine was added to aliquot #2. 1.2 mg (2 μmol) of A$_{tri}$-OCH$_2$CH$_2$CH$_2$NH$_2$ in 500 μl DMSO containing additional 5 μl of triethylamine was added to aliquot #3. The mixtures were incubated at 37° C. for 24 hr. All reaction mixtures were kept at −20° C.

Example 2

Derivatives of p-Nitrophenyl-Activated Polyacrylic Acid

A solution of 5.7 mg (20 mg-eq.) pNPA$^{30}$ in 500 μl DMSO was added to 0.2 μmol of fluorescein-cadaverine in 44 μl of DMSO followed by 6 µl triethylamine and incubated at 37° C. overnight. The mixture was then divided into 3 equal aliquots identified as #1, #2 and #3. Nothing was added to aliquot #1 (negative control). 1.1 mg (2 µmol) of $B_{tri}$—$OCH_2CH_2CH_2NH_2$ in 500 µl DMSO containing additional 5 µl of triethylamine was added to aliquot #2. 1.2 mg (2 µmol) of $A_{tri}$-$OCH_2CH_2CH_2NH_2$ in 500 µl DMSO containing additional 5 µl of triethylamine was added to aliquot #3. The mixtures were incubated at 37° C. for 24 hr. All reaction mixtures were kept at −20° C.

Example 3

Derivatives of PEGylated N-Hydroxysuccinimide-Activated Polyacrylic Acid

A solution of 5.1 mg (30 mg-eq.) pNSA$^{2m}$ in 500 µl DMSO was added to 0.2 µmol of fluorescein-cadaverine and 0.02 to 0.20 aminated PEG in a total volume of 44 µl of DMSO followed by 6 µl triethylamine and incubated at 37° C. overnight. The mixture was then divided into 3 equal aliquots identified as #1, #2 and #3. Nothing was added to aliquot #1 (negative control). 1.1 mg (2 µmol) of $B_{tri}$—$OCH_2CH_2CH_2NH_2$ in 500 µl DMSO containing additional 5 µl of triethylamine was added to aliquot #2. 1.2 mg (2 µmol) of $A_{tri}$-$OCH_2CH_2CH_2NH_2$ in 500 µl DMSO containing additional 5 µl of triethylamine was added to aliquot #3. The mixtures were incubated at 37° C. for 24 hr. All reaction mixtures were kept at −20° C.

Example 4

Derivatives of PEGylated p-Nitrophenyl-Activated Polyacrylic Acid

A solution of 5.7 mg (30 mg-eq.) pNPA$^{30}$ in 500 µl DMSO was added to 0.3 µmol of fluorescein-cadaverine and 0.03 to 0.30 aminated PEG in a total volume of 44 µl of DMSO followed by 6 µl triethylamine and incubated at 37° C. overnight. The mixture was then divided into 3 equal aliquots identified as #1, #2 and #3. Nothing was added to aliquot #1 (negative control). 1.1 mg (2 µmol) of $B_{tri}$—$OCH_2CH_2CH_2NH_2$ in 500 µl DMSO containing additional 5 µl of triethylamine was added to aliquot #2. 1.2 mg (2 µmol) of $A_{tri}$-$OCH_2CH_2CH_2NH_2$ in 500 µl DMSO containing additional 5 µl of triethylamine was added to aliquot #3. The mixtures were incubated at 37° C. for 24 hr. All reaction mixtures were kept at −20° C.

Example 5

Derivatives of Aminated p-Nitrophenyl-Activated Polyacrylic Acid

A solution of 7.8 mg (41.1 mg-eq.) pNPA$^{30}$ in 400 µl DMSO was added to 0.42 to 1.2 µmol of 8-trifluoroacetyl-protected lysine in 100 p. 1 of DMSO. The mixture was then divided into 3 equal aliquots identified as #1, #2 and #3. Nothing was added to aliquot #1 (negative control). 1.5 mg (2.7 mal) of $B_{tri}$—$OCH_2CH_2CH_2NH_2$ in 100 µl DMSO was added to aliquot #2. 1.6 mg (2.7 µmol) of $A_{tri}$-$OCH_2CH_2CH_2NH_2$ in 100 µl DMSO was added to aliquot #3. The mixtures were incubated at 40° C. for 24 h. A volume of 27 µl of ethanolamine was then added to each aliquot and the reaction performed at 37° C. for 24 hr. A volume of 300 µl of double distilled water was added and the mixtures then kept at room temperature overnight. The by-products of the reaction were dialyzed against PBS followed by water and the conjugates were lyophilized.

Example 6

Derivatives of Aminated N-Hydroxysuccinimide-Activated Polyacrylic Acid

A solution of 6.9 mg (41.1 mg-eq.) pNSA$^{2000}$ in 400 µl DMSO was added to 0.42 to 1.2 µmol of c-trifluoroacetyl-protected lysine in 100 µl of DMSO. The mixture was then divided into 3 equal aliquots identified as #1, #2 and #3. Nothing was added to aliquot #1 (negative control). 1.5 mg (2.7 µmol) of $B_{tri}$—$OCH_2CH_2CH_2NH_2$ in 100 µl DMSO was added to aliquot #2. 1.6 mg (2.7 µmol) of $A_{tri}$-$OCH_2CH_2CH_2NH_2$ in 100 µl DMSO was added to aliquot #3. The mixtures were incubated at 40° C. for 24 h. A volume of 27 µl of ethanolamine was then added to each aliquot and the reaction performed at 37° C. for 24 hr. A volume of 300 µl of double distilled water was added and the mixtures then kept at room temperature overnight. The by-products of the reaction were dialyzed against PBS followed by water and the conjugates were lyophilized.
Fabrication of glycan arrays Example 7

Glycan Array Consisting of Two Glycans and Negative Controls

Four activated polyacrylic glycoconjugates ($A_{tri}$ and $B_{tri}$ containing fluorescein derivatives of pNSA$^{2000}$ (Example 1), $A_{tri}$ and $B_{tri}$ containing fluorescein derivatives of pNPA$^{30}$ (Example 2), $A_{tri}$ and $B_{tri}$ containing PEGylated pNSA$^{2000}$ (Example 3) and $A_{tri}$ and $B_{tri}$ containing PEGylated pNPA$^{30}$ (Example 4)) and two corresponding carbohydrate-free activated polymers were diluted with DMSO, containing 1% (v/v) Et$_3$N, up to 10 and 50 µM glycan concentrations. All six polymers were printed onto aminated glass slides at room temperature in 6 replicates using a 32-pin manual arrayer V&P Scientific (USA) or by a contact robotic system (ArrayIt). The printed slides were incubated for 1 h at 37° C. in an atmosphere of DMSO containing 1% (v/v) Et$_3$N. The incubated slide was scanned for the presence of fluorescence using a microarray scanner (ScanArray Express, Perkin Elmer (USA)) with 5 µm-scan resolution (laser power—90%, PMT gain—70%). The fluorescent image was saved in the form of a TIFF file and used as a control for further steps. Active groups of the polymers were quenched with 50 mM ethanolamine in 50 mM borate buffer, pH 9.2, for 1 h at room temperature. The glycochip was then rinsed with water and dried by centrifuging. The slide was scanned again and saved as a TIFF file for software analysis (ScanArray Express 3.0), immobilization degree estimation and quality control.

Example 8

Glycan Array Containing Aminated Polyacrylamide Conjugates

Aminated polyacrylic glycoconjugates (Example 5 and Example 6) and two corresponding carbohydrate-free activated polymers were diluted with 150 mM phosphate buffer (pH 8.5) containing 0.005% CHAPS or 0.001% Tween™ 20 to 10 and 50 µM glycan concentrations. All polymers were printed onto an epoxy-activated glass slide at 50% humidity in 6 replicates using a 32-pin manual arrayer (V&P Scientific (USA)) or by a contact robotic system (ArrayIt). The printed slides were incubated for 1 h in a humidifying chamber (at 75% humidity) at room temperature. The slide was scanned for the presence of fluorescence using a microarray scanner (ScanArray Express, Perkin Elmer (USA)) with 5 µm scan resolution (laser power 90%, PMT gain 70%). The fluorescent image was saved in the form of a TIFF file and used as a control for further steps. Active groups on the slide were quenched with 50 mM ethanolamine in 50 mM borate buffer (pH 9.2) for 1 h at room temperature. The glycochip was then rinsed with water and dried by centrifuging. The slide was scanned again and saved as a TIFF file for software analysis (ScanArray Express 3.0), immobilization degree estimation and quality control.

Glycochip Staining by Glycan-Binding Proteins

Example 9

Lectin or Antibodies

The glycochip was humidified in PBS containing 0.1% Tween™ 20 for 15 min just before vortexing the diluted sample. An appropriate sample volume of 1 to 100 µg/ml solution of lectin or antibodies in PBS containing 0.1% Tween™ 20 (and 3% of BSA in the case of antibodies) were applied to the slide and incubated in a humidifying chamber (at 75% humidity) under gentle rocking for 1 h at room temperature or 37° C. The slide was washed with PBS containing 0.1% Tween™ 20 and then 2 times with a PBS 0.001% Tween™ 20 solution. The washed slide was labelled by addition of appropriate fluorophore streptavidin in case of biotinylated lectins and antibodies or otherwise fluorophore labelled secondary antibodies in PBS containing 0.1% Tween™ 20 (typical dilution 1:1000) and incubation at 75% humidity under gentle rocking for 1 h at room temperature. After washing with PBS containing 0.1% Tween™ 20, then two times with a PBS 0.001% Tween™ 20 solution followed by water, fluorescence intensity was measured using microarray scanner (ScanArray Express, Perkin Elmer (USA)) with 5 µm scan resolution (laser power 90%, PMT gain 70%). The fluorescent image was saved in the form of a TIFF file and analyzed using software (ScanArray Express 3.0).

Example 10

Serum Incubation

The glycochip was humidified in PBS containing 0.1% TWEEN™ 20 for 15 min just before vortexing the diluted sample. A sample of serum (human, mouse, etc.) was diluted up to 1:100 in PBS containing 3% BSA, 1% Tween™ 20 and the solution vortexed and pre-incubated for 15 min at 37° C. followed by centrifuging (3 min, 12500 rpm). Appropriate serum sample volumes were added to the slide and incubated for 1.5 h at 75% humidity under gentle rocking at 37° C. The slide was washed with PBS containing 0.1% Tween™ 20, then 2 times with a PBS, 0.001% Tween™ 20 solution. Fluorophore labelled secondary antibodies (anti IgG, M, A or their cocktail) typically diluted 1:200 in PBS containing 3% BSA and 0.1% Tween™ 20 were then added to the chip and incubated at 75% humidity under gentle rocking, for 1 h at 37° C. After washing with PBS containing 0.1% Tween™ 20, then 2 times with a PBS 0.001% Tween™ 20 solution followed by water and drying by centrifuging, fluorescence intensity was measured using a microarray scanner (SeanArray Express, Perkin Elmer (USA)) with 5 µm scan resolution (laser power 90%, PMT gain 70%). The fluorescent image was saved in the form of a TIFF file and analyzed using software (ScanArray Express 3.0).

The glycan arrays can be scanned at different qualities and powers. By varying the PMT, laser power, and resolution, the instrument can produce an image with as many signals as possible within its dynamic range.

Results

The non-quantitative immobilization of activated $pNPA^{30}$ and $pNSA^{2000}$ on aminated polystyrene has previously been demonstrated [Shilova et al (2005) *High molecular weight neoglycoconjugates for solid phase assays* Glycoconjugate J 22, 43-51]. Glycan arrays employing this method were also found to present a background signal unacceptable for assays.

Figure 4:
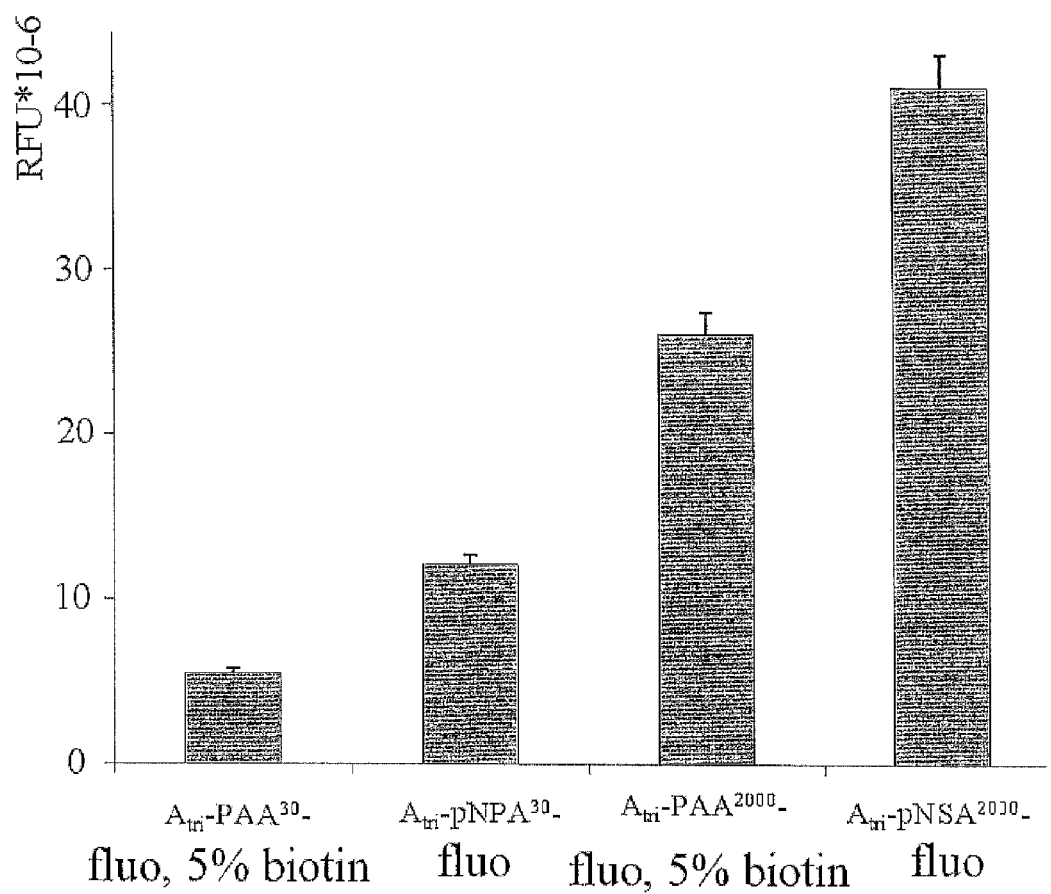
FIG. 4. Comparison of signals from: (i) fluorescently labelled and biotinylated, ω-aminoalkylglycan (A$_{tri}$) derivatives of polyacrylates immobilized on avidinylated glass slides; and (ii) fluorescently labelled, ω-aminoalkylglycan (A$_{tri}$) derivatives of polyacrylamides immobilized on aminated glass slides. Glycan array development was performed using fluorescently labelled secondary antibodies. Background (signal from dots containing polyacrylamide without carbohydrate ligands) was subtracted.

The method of the invention exploits the observation that the reaction between an ω-aminoalkylglycan and activated polyacrylamide polymers such as $pNPA^{30}$ and $pNSA^{2000}$ proceeds quantitatively in DMSO and DMFA under mild conditions. Importantly quantitative modification of the polymer up to 20% mol occurs at both microscale and semi-preparative (100 to 1000 mg scales). The balance of the active groups (80% mol) may then be exploited to immobilize the glycopolymer on an aminated glass substrate under similarly mild conditions. The mild conditions permit the prior quantitative labeling of the polymer with a range of reporter groups such as fluorophores, using known bioconjugation chemistry. The fluorophore is selected to complement the fluorogenic detection of ligand binding to the bioarray. The degree of immobilization of fluorescently labeled activated glycopolymers has been monitored by measurement of the fluorescence intensity immediately after printing and after washing. The ratio of the fluorescence intensity signal before and after washing reflects the degree of immobilization. The ratio indicated that immobilization of the activated glycopolymers proceeded with a yield of about 100% (within the scanning error range). The quantitative immobilization of the activated glycopolymer was achievable across a concentration range of two orders of magnitude (up to 100-fold difference). The ability to immobilize glycans capable of participating in multivalent interactions at a range of concentrations is an important feature of glycan array design and fabrication. The quantitative nature of the first and second steps of the method of the invention was demonstrated for both bulky, branched and negatively charged glycans as well as small neutral glycans such as $A_{tri}$ and $B_{tri}$. Further, it has now been demonstrated that the unacceptable background signal of the glycan arrays of Shilova et al (2005) [*High molecular weight neoglycoconjugates for solid phase assays* Glycoconjugate J 22, 43-51] is avoided or at least reduced to acceptable levels by the method of the invention. The results presented in FIG. 4 demonstrate the improved signal detection obtained when aminated glass is selected as the substrate. In addition to the foregoing advantages, the selection of aminated or epoxylated slides also avoids some of the limitations of fabricating glycan arrays as previously described [Bouin and Chinarev (2008) Bioanalytic systems and methods Publ. no. US 2008/0076137]. Aminated or epoxylated substrates may be manufactured more cheaply and consistently than avidinylated substrates, small variations in the degree of amination of the substrate having less effect on immobilization of the glycopolymer than variations in the quality of avidin or streptavidin and attachment used in the manufacture of avidinylated surfaces. A comparison of the fluorescent signal obtained for glycopolymers immobilized via biotin-streptavidin interaction versus covalent attachment is presented (FIG. 4).

Although the invention has been described with reference to embodiments or examples it should be appreciated that variations and modifications may be made to these embodiments or examples without departing from the scope of the invention. Where known equivalents exist to specific features, such equivalents are incorporated as if specifically referred to in this specification.

INDUSTRIAL APPLICABILITY

The invention provides a method of fabricating glycan arrays.

The invention claimed is:

1. A method of fabricating a glycan array comprising the steps of:
   Quantitatively reacting an ω-aminoalkylglycan with a fluorescently-labelled activated polymer of an acrylic acid derivative to provide a glycoconjugated, fluorescently-labelled polymer or copolymer of the acrylic acid derivative;
   Reacting the glycoconjugated, fluorescently-labelled polymer or copolymer of the acrylic acid derivative with a trifuoroacetyl-protected lysine to provide a lysine group-attached, glycoconjugated, fluorescently-labelled polymer or copolymer of the acrylic acid derivative; and
   Covalently attaching the lysine group-attached, fluorescently-labelled, glycoconjugated polymer or copolymer of the acrylic acid derivative to a functionalized substrate, where the functionalized substrate is an epoxylated substrate.

2. The method of claim 1 where the ω-aminoalkylglycan is selected from the group consisting of: ω-aminoalkyl O- or N-derivatives of a glycan.

3. The method of claim 2 where the ω-aminoalkylglycan is selected from the group consisting of: ω-amino-$C_{1-6}$-alkyl O— or N-derivatives of a glycan.

4. The method of claim 3 where the ω-amino-$C_{1-6}$-alkyl O— or N-derivatives of a glycan is selected from the group consisting of: Glyc-OCH$_2$CH$_2$CH$_2$NH$_2$, Glyc-OCH$_2$CH$_2$NH$_2$ and Glyc-NHCOCH$_2$NH$_2$.

5. The method of claim 1 where the glycan (Glyc) is selected from the group consisting of: Galα, Glcα, Manα, GalNAcα, Fucα, Rhaα, Neu5Acα, Neu5Acα, Neu5Acβ, Galβ, Glcβ, Manβ, GalNAcβ, GlcNAcβ, GlcNAcβ, GlcNGcβ, Galβ1-4GlcNAcβ1-3(Galβ1-4GlcNAcβ1-6)GalNAcα, GlcNAcβ1-3(GlcNAcβ1-6)GlcNAcβ1-4GlcNAcβ, Gal[3OSO3, 6OSO3]β1-4GlcNAc[6OSO3]β, Gal[3OSO3, 6OSO3]β1-4GlcNAcβ, Gal[3OSO3]β1-4Glcβ, Gal[3OSO3]β1-4Glc[6OSO3]β, Gal[3OSO3]β1-4Glc[6OSO3]β, Gal[3OSO3]β1-3(Fucα1-4)GlcNAcβ, Gal[3OSO3]β1-3GalNAcα, Gal[3OSO3]β1-3GlcNAcβ, Gal[3OSO3]β1-4(Fucα1-3)GlcNAcβ, Gal[6OSO3]β1-4GlcNAcβ[6OSO3]β, Gal[3OSO3]β1-4GlcNAcβ, Gal[3OSO3]β1-4GlcNAcβ, Gal[3OSO3]β, Gal[4OSO3, 6OSO3]β1-4GlcNAc, Gal[4OSO3]β1-4GlcNAcβ, Man[6-H2PO3]α, Gal[6OSO3]β1-4Glcβ, Gal[6OSO3]β1-4Glcβ, Gal[6OSO3]β1-4GlcNAcβ, Gal[6OSO3]β1-4Glc[6OSO3]β, Neu5Acα2-3Gal[6OSO3]β1-4GlcNAcβ, GlcNAc[6OSO3]β,Neu5Ac[9Ac]α, Neu5Ac[9Ac]α2-6Galβ1-4GlcNAcβ, Manα1-3(Manα1-6)Manβ1-4GlcNAcβ1-4GlcNAcβ, GlcNAcβ1-2Manα1-3(GlcNAcβ1-2Manα1-6)Manβ1-4GlcNAcβ1-4GlcNAcβ, Galβ1-4GlcNAcβ1-2Manα1-3(Galβ1-4GlcNAcβ1-2Manα1-6)Manβ1-4GlcNAcβ1-4GlcNAcβ, Neu5Acα2-3Galβ1-4GlcNAcβ1-2Manα1-3(Neu5Acα2-3Galβ1-4GlcNAcβ1-2Manα1-6)Manβ1-4GlcNAcβ1-4GlcNAcβ, Neu5Acα2-6Galβ1-4GlcNAcβ1-2Manα1-3(Neu5Acα2-6Galβ1-4GlcNAcβ1-2Manα1-6)Manβ1-4GlcNAcβ1-4GlcNAcβ, Fucα1-2Galβ1-3GalNAcβ1-3Galα, Fucα1-2Galβ1-3GalNAcβ1-3Galα1-4Galβ1-4Glcβ, Fucα1-2Galβ1-3(Fucα1-4)GlcNAcβ, Fucα1-2Galβ1-3GalNAcα, Fucα1-2Galβ1-3GalNAcβ1-4(Neu5Acα2-3)Galβ1-4Glcβ, Fucα1-2Galβ1-3GalNAcβ1-4(Neu5Acα2-3)Galβ1-4Glcβ, Fucα1-2Galβ1-3GlcNAcβ1-3Galβ1-4Glcβ, Fucα1-2Galβ1-3Galβ1-4Glcβ, Fucα1-2Galβ1-3GlcNAcβ, Fucα1-2Galβ1-3GlcNAcβ, Fucα1-2Galβ1-4(Fucα1-3)GlcNAcβ1-3Galβ1-4(Fucα1-3)GlcNAcβ, Fucα1-2Galβ1-4(Fucα1-3)GlcNAcβ1-3Galβ1-4(Fucα1-3)GlcNAcβ1-3Galβ1-4(Fucα1-3) GlcNAcβ, Fucα1-2Galβ1-4(Fucα1-3)GlcNAcβ, Fucα1-2Galβ1-4(Fucα1-3) GlcNAcβ, Fucα1-2Galβ1-4GlcNAcβ1-3Galβ1-4GlcNAcβ, Fucα1-2Galβ1-4GlcNAcβ1-3Galβ1-4GlcNAcβ1-3Galβ1-4GlcNAcβ, Fucα1-2Galβ1-4GlcNAcβ, Fucα1-2Galβ1-4GlcNAcβ, Fucα1-2Galβ1-4Glcβ, Fucα1-2Galβ, Fucα1-2GlcNAcβ, Fucα1-3GlcNAcβ, Fucα1-4GlcNAcβ, Fucα1-3GlcNAcβ, GalNAcα1-3(Fucα1-2)Galβ1-3GlcNAcβ, GalNAcα1-3(Fucα1-2)Galβ1-4(Fucα1-3)GlcNAcβ, GalNAcα1-3(Fucα1-2)Galβ1-4GlcNAcβ, GalNAcα1-3(Fucα1-2)Galβ1-4GlcNAcβ, GalNAcα1-3(Fucα1-2)Galβ1-4Glcβ, GalNAcα1-3(Fucα1-2)Galβ, GalNAcα1-3GalNAcβ, GalNAcα1-3Galβ, GalNAcα1-4(Fucα1-2)Galβ1-4GlcNAcβ, GalNAcβ1-3GalNAcα, GalNAcβ1-3(Fucα1-2)Galβ, GalNAcβ1-3Galα1-4Galβ1-4GlcNAcβ, GalNAcβ1-4(Fucα1-3)GlcNAcβ, GalNAcβ1-4GlcNAcβ, GalNAcβ1-4GlcNAcβGalα1-2Galβ, Galα1-3(Fucα1-2)Galβ1-3GlcNAcβ, Galα1-3(Fucα1-2)Galβ1-4(Fucα1-3)GlcNAcβ, Galα1-3(Fucα1-2)Galβ1-4GlcNAcβ, Galα1-3(Fucα1-2)Galβ1-4Glcβ, Galα1-3(Fucα1-2)Galβ, Galα1-3(Galα1-4)Galβ1-4GlcNAcβ, Galα1-3GalNAcα, Galα1-3GalNAcβ, Galα1-3Galβ1-4(Fucα1-3) GlcNAcβ, Galα1-3Galβ1-3GlcNAcβ, Galα1-3Galβ1-4GlcNAcβ, Galα1-3Galβ1-4Glcβ, Galα1-3Galβ, Galα1-4(Fucα1-2)Galβ1-4GlcNAcβ, Galα1-4Galβ1-4GlcNAcβ, Galα1-4Galβ1-4GlcNAcβ, Galα1-4Galβ1-4Glcβ, Galα1-4GlcNAcβ, Galα1-6Glcβ, Galβ1-2Galβ, Galβ1-3(Fucα1-4) GlcNAcβ1-3Galβ1-4(Fucα1-3)GlcNAcβ, Galβ1-3(Fucα1-4)GlcNAcβ1-3Galβ1-4GlcNAcβ, Galβ1-3(Fucα1-4)GlcNAcβ, Galβ1-3(Fucα1-4) GlcNAcβ, Galβ1-3(Fucα1-4)GlcNAcβ, Galβ1-3(Galβ1-4GlcNAcβ1-6) GalNAcα, Galβ1-3(GlcNAcβ1-6) GalNAcα, Galβ1-3(Neu5Acα2-6) GalNAcα, Galβ1-3(Neu5Acβ2-6)GalNAcα, Galβ1-3(Neu5Acα2-6) GlcNAcβ1-4Galβ1-4Glcβ, Galβ1-3GalNAcα, Galβ1-3GalNAcβ, Galβ1-3GalNAcβ1-3Galα1-4Galβ1-4Glcβ, Galβ1-3GalNAcβ1-4(Neu5Acα2-3) Galβ1-4Glcβ, Galβ1-3GalNAcβ1-4Galβ1-4Glcβ, Galβ1-3Galβ, Galβ1-3GlcNAcβ1-3Galβ1-4GlcNAcβ, Galβ1-3GlcNAcβ1-3Galβ1-4Glcβ, Galβ1-3GlcNAcβ, Galβ1-3GlcNAcβ, Galβ1-4(Fucα1-3)GlcNAcβ, Galβ1-4(Fucα1-3) GlcNAcβ, Galβ1-4Glc[6OSO3]β, Galβ1-4Glc[6OSO3]β, Galβ1-4GalNAcα1-3(Fucα1-2)Galβ1-4GlcNAcβ, Galβ1-4GalNAcβ1-3(Fucα1-2) Galβ1-4GlcNAcβ, Galβ1-4GlcNAcβ1-3(Galβ1-4GlcNAcβ1-6)GalNAcα, Galβ1-4GlcNAcβ1-3GalNAcα, Galβ1-4GlcNAcβ1-3Galβ1-4 (Fucα1-3) GlcNAcβ1-3Galβ1-4(Fucα1-3)GlcNAcβ, Galβ1-4GlcNAcβ1-3Galβ1-4GlcNAcβ, Galβ1-4GlcNAcβ1-3Galβ1-4GlcNAcβ, Galβ1-4GlcNAcβ1-3Galβ1-4GlcNAcβ1-3Galβ1-4GlcNAcβ, Galβ1-4Glcβ, Galβ1-4GlcNAcβ1-6(Galβ1-3)GalNAcα, Galβ1-4GlcNAcβ1-6GalNAcα, Galβ1-4GlcNAcβ, Galβ1-4GlcNAcβ, Galβ1-4Glcβ, Galβ1-4Glcβ, GlcNAcβ1-

3Galβ1-4GlcNAcβ, GlcNAcα1-6Galβ1-4GlcNAcβ, GlcNAcβ1-2Galβ1-3GalNAcα, GlcNAcβ1-3(GlcNAcβ1-6)GalNAcα, GlcNAcβ1-3(GlcNAcβ1-6)Galβ1-4GlcNAcβ, GlcNAcβ1-3GalNAcα, GlcNAcβ1-3Galβ, GlcNAcβ1-3Galβ1-3GalNAcα, GlcNAcβ1-3Galβ1-4GlcNAcβ, GlcNAcβ1-3Galβ1-4GlcNAcβ, GlcNAcβ1-3Galβ1-4GlcNAcβ1-3Galβ1-4GlcNAcβ, GlcNAcβ1-3Galβ1-4Glcβ, GlcNAcβ1-4MDPLys (bacterial cell wall), GlcNAcβ1-4(GlcNAcβ1-6)GalNAcα, GlcNAcβ1-4Galβ1-4GlcNAcβ, GlcNAcβ1-4GlcNAcβ1-4GlcNAcβ1-4GlcNAcβ1-4GlcNAcβ1-4GlcNAcβ, GlcNAcβ1-4GlcNAcβ1-4GlcNAcβ1-4GlcNAcβ1-4GlcNAcβ, GlcNAcβ1-4GlcNAcβ1-4GlcNAcβ, GlcNAcβ1-6(Galβ1-3)GalNAcα, GlcNAcβ1-6GalNAcα, GlcNAcβ1-6Galβ1-4GlcNAcβ, Glcα1-4Glcβ, Glcα1-4Glcα, Glcα1-6Glcα1-6Glcβ, Glcβ1-4Glcβ, Glcβ1-6Glcβ, GlcAα, GlcAβ, GlcAβ1-3Galβ, GlcAβ1-6Galβ, KDNα2-3Galβ1-3GlcNAcβ, KDNα2-3Galβ1-4GlcNAcβ, Manα1-2Manα1-2Manα1-3Manα, Manα1-2Manα1-3(Manα1-2Manα1-6)Manα, Manα1-2Manα1-3Manα, Manα1-6(Manα1-2Manα1-3) Manα1-6(Manα1-2Manα1-3)Manβ1-4GlcNAcβ1-4GlcNAcβ, Manα1-2Manα1-6(Manα1-3)Manα1-6(Manα1-2Manα1-2Manα1-3)Manβ1-4GlcNAcβ1-4GlcNAcβ, Manα1-2Manα1-2Manα1-3[Manα1-2Manα1-3(Manα1-2Manα1-6)Manα1-6]Manβ1-4GlcNAcβ1-4GlcNAcβ, Manα1-3(Manα1-6)Manα, Manα1-3(Manα1-2Manα1-2Manα1-6)Manα, Manα1-2Manα1-3(Manα1-3(Manα1-6)Manα1-6) Manβ1-4GlcNAcβ1-4GlcNAcβ, Manα1-3(Manα1-3(Manα1-6)Manα1-6) Manβ1-4GlcNAcβ1-4GlcNAcα, Manβ1-4GlcNAcβ,Neu5Acα2-3(Galβ1-3GalNAcβ1-4)Galβ1-4Glcβ, Neu5Acα2-3Galβ1-3GalNAcα, Neu5Acα2-8Neu5Acα2-8Neu5Acα2-8Neu5Acα2-3(GalNAcβ1-4)Galβ1-4Glcβ, Neu5Acα2-8Neu5Acα2-8Neu5Acα2-3(GalNAcβ1-4)Galβ1-4Glcβ, Neu5Acα2-8Neu5Acα2-8Neu5Acα2-3Galβ1-4Glcβ, Neu5Acα2-8Neu5Acα2-3(GalNAcβ1-4)Galβ1-4Glcβ, Neu5Acα2-8Neu5Acα2-8Neu5Acα, Neu5Acα2-3Gal[6OSO3]β1-4(Fucα1-3)GlcNAcβ, Neu5Acα2-3(GalNAcβ1-4)Galβ1-4GlcNAcβ, Neu5Acα2-3(GalNAcβ1-4)Galβ1-4GlcNAcβ, Neu5Acα2-3(GalNAcβ1-4) Galβ1-4Glcβ, Neu5Acα2-3(Neu5Acα2-3Galβ1-3GalNAcβ1-4)Galβ1-4Glcβ, Neu5Acα2-3(Neu5Acα2-6)GalNAcα, Neu5Acα2-3GalNAcα, Neu5Acα2-3GalNAcβ1-4GlcNAcβ, Neu5Acα2-3Gal[6OSO3]β1-3GlcNAc, Neu5Acα2-3Galβ1-3(Fucα1-4) GlcNAcβ, Neu5Acα2-3Galβ1-3(Fucα1-4) GlcNAcβ1-3Galβ1-4(Fucα1-3)GlcNAcβ, Neu5Acα2-3Galβ1-3(Neu5Acα2-3Galβ1-4)GlcNAcβ, Neu5Acα2-3Galβ1-3GalNAc[6OSO3]α, Neu5Acα2-3(Neu5Acα2-6)GalNAcα, Neu5Acα2-3Galβ, Neu5Acα2-3Galβ1-3GalNAcβ1-3Galβ1-4Galβ1-4Glcβ, Neu5Acα2-3Galβ1-3GalNAcβ1-3Galβ1-4GlcNAcβ, Neu5Acα2-3Galβ1-3GlcNAcβ, Neu5Acα2-3Galβ1-3GlcNAcβ, Neu5Acα2-3Galβ1-4GlcNAc[6OSO3]β, Neu5Acα2-3Galβ1-4(Fucα1-3)GlcNAc[6OSO3]β, Neu5Acα2-3Galβ1-4(Fucα1-3)GlcNAcβ1-3Galβ1-4(Fucα1-3)GlcNAcβ1-3Galβ1-4(Fucα1-3)GlcNAcβ, Neu5Acα2-3Galβ1-4(Fucα1-3)GlcNAcβ, Neu5Acα2-3Galβ1-4(Fucα1-3)GlcNAcβ, Neu5Acα2-3Galβ1-4(Fucα1-3) GlcNAcβ1-3Galβ, Neu5Acα2-3Galβ1-4(Fucα1-3)GlcNAcβ1-3Galβ1-4GlcNAcβ, Neu5Acα2-3Galβ1-4GlcNAcβ1-3Galβ1-4(Fucα1-3)GlcNAc, Neu5Acα2-3Galβ1-4GlcNAcβ1-3Galβ1-4GlcNAcβ1-3Galβ1-4GlcNAcβ, Neu5Acα2-3Galβ1-4GlcNAcβ, Neu5Acα2-3Galβ1-4GlcNAcβ, Neu5Acα2-3Galβ1-4GlcNAcβ1-3Galβ1-4GlcNAcβ, Neu5Acα2-3Galβ1-4Glcβ, Neu5Acα2-3Galβ1-4Glcβ, Neu5Acα2-6(Galβ1-3)GalNAcα, Neu5Acα2-6GalNAcα, Neu5Acα2-6GalNAcβ1-4GlcNAcβ, Neu5Acα2-6Galβ1-4GlcNAc[6OSO3]β, Neu5Acα2-6Galβ1-4GlcNAcβ, Neu5Acα2-6Galβ1-4GlcNAcβ, Neu5Acα2-6Galβ1-4GlcNAcβ1-3Galβ1-4(Fucα1-3)GlcNAcβ1-3Galβ1-4(Fucα1-3)GlcNAcβ, Neu5Acα2-6Galβ1-4GlcNAcβ1-3Galβ1-4GlcNAcβ, Neu5Acα2-6Galβ1-4Glcβ, Neu5Acα2-6Galβ1-4Glcβ, Neu5Acα2-6Galβ, Neu5Acα2-8Neu5Acα, Neu5Acα2-8Neu5Acα2-3Galβ1-4Glcβ, Neu5Acβ2-6GalNAcα, Neu5Acβ2-6Galβ1-4GlcNAcβ, Neu5Acβ2-6(Galβ1-3) GalNAcα, Neu5Gcα2-3Galβ1-3(Fucα1-4)GlcNAcβ, Neu5Gcα2-3Galβ1-3GlcNAcβ, Neu5Gcα2-3Galβ1-4(Fucα1-3)GlcNAcβ, Neu5Gcα2-3Galβ1-4GlcNAcβ, Neu5Gcα2-3Galβ1-4Glcβ, Neu5Gcα2-6GalNAcα, Neu5Gcα2-6Galβ1-4GlcNAcβ and Neu5Gcα.

6. The method of claim 1 where the fluorescently-labelled activated polymer of the acrylic acid derivative is selected from the group consisting of: poly(4-nitrophenyl acrylate) and poly(N-oxysuccinimidyl acrylate).

7. The method of claim 1 where the fluorophore of the fluorescent label is selected from the consisting of: fluorophores of fluorescein.

8. The method of claim 7 where the fluorescent label is fluorescein cadaverine (fluo).

9. The method of claim 8 where the glycoconjugated, fluorescently-labelled polymer or copolymer of the acrylic acid derivative comprises fluorophore at no more than 1 mole %.

10. The method of claim 1 where the glycoconjugated, fluorescently-labelled polymer or copolymer of the acrylic acid derivative comprises glycan in the range 0.1 to 40 mole %.

11. The method of claim 1 where the covalently attaching is via a plurality of bonds.

12. The method of claim 1 where the substrate is selected from the group consisting of: glass and plastic.

13. The method of claim 12 where the substrate is selected from the group consisting of: glass and plastic slides.

14. A glycan array comprising ω-aminoalkylglycan covalently attached to a functionalized substrate via a fluorescently-labelled polymer or copolymer of an acrylic acid derivative, where the functionalized substrate is an epoxylated substrate, and wherein the ω-aminoalkylglycan is also lysine-group attached by being reacted with a trifuoroacetyl-protected lysine.

15. The glycan array of claim 14 where the glycan array has the formula:

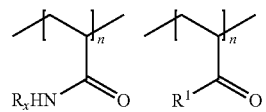

where x is an integer from 1 to n and $R_x$ is selected from the alkylglycan and at least one from the group consisting of: lysine, aminated PEG or substrate; $R^1$ is $NH_2$, OH or $HOCH_2CH_2NH$.

16. The glycan array of claim 14 where the fluorophore of the fluorescent label is selected from the group consisting of: fluorophores of fluorescein.

17. The glycan array of claim 16 where the fluorescent label is fluorescein cadaverine (fluo).

18. The glycan array of claim 14 where the glycoconjugated polymer or copolymer of an acrylic acid derivative comprises fluorophore at no more than 1 mole %.

19. The glycan array of claim 14 where the glycoconjugated polymer or copolymer of an acrylic acid derivative comprises glycan in the range 0.1 to 40 mole %.

20. The glycan array of claim 14 where the covalently attaching is via a plurality of bonds.

21. The glycan array of claim 14 where the substrate is selected from the group consisting of: glass and plastic.

22. The glycan array of claim 21 where the substrate is selected from the group consisting of: glass and plastic slides.

* * * * *